United States Patent [19]

Minami et al.

[11] Patent Number: 5,576,458
[45] Date of Patent: Nov. 19, 1996

[54] PROCESS FOR PREPARING ORGANIC CARBOXYLIC ACID

[75] Inventors: Takeshi Minami; Kazuhiko Hamato; Kenji Shimokawa; Yoshimi Shiroto, all of Kanagawa-ken, Japan

[73] Assignee: Chiyoda Corporation, Yokohama, Japan

[21] Appl. No.: 407,612

[22] Filed: Mar. 21, 1995

[30] Foreign Application Priority Data

Mar. 25, 1994 [JP] Japan .................................. 6-077826
Oct. 21, 1994 [JP] Japan .................................. 6-282719

[51] Int. Cl.⁶ ................................................ C07C 45/50
[52] U.S. Cl. ........................ 562/519; 562/522; 562/607
[58] Field of Search ................................ 562/519, 522, 562/607

[56] References Cited

U.S. PATENT DOCUMENTS

| | | | |
|---|---|---|---|
| 4,328,125 | 5/1982 | Drago et al. | 560/519 |
| 5,227,520 | 7/1993 | Cooper et al. | 560/519 |
| 5,364,963 | 11/1994 | Minami et al. | 560/519 |
| 5,442,107 | 8/1995 | Beevor et al. | 560/519 |

FOREIGN PATENT DOCUMENTS 567331  10/1993  European Pat. Off. .

OTHER PUBLICATIONS

Abstract of Japanese Patent Laid–Open Publication No. 10680/1978.

*Primary Examiner*—Paul J. Killos
*Attorney, Agent, or Firm*—Armstrong, Westerman, Hattori, McLeland & Naughton

[57] ABSTRACT

In the production step, alcohol is reacted with carbon monoxide in a reaction solvent in the presence of a rhodium-containing solid catalyst obtained by immobilizing rhodium in an insoluble carrier (I) containing a pyridine ring in its resin structure and an alkyl iodide containing an alkyl group of 1 to 5 carbon atoms, to produce a reaction product having a water content of 0.5 to 10% by weight; and in the subsequent removing step, an organic carboxylic acid is separated and recovered from the reaction product, and the recovered organic carboxylic acid is contacted with an insoluble carrier (II) containing a pyridine ring in its resin structure, to remove an iodide contained in the organic carboxylic acid.

14 Claims, 1 Drawing Sheet

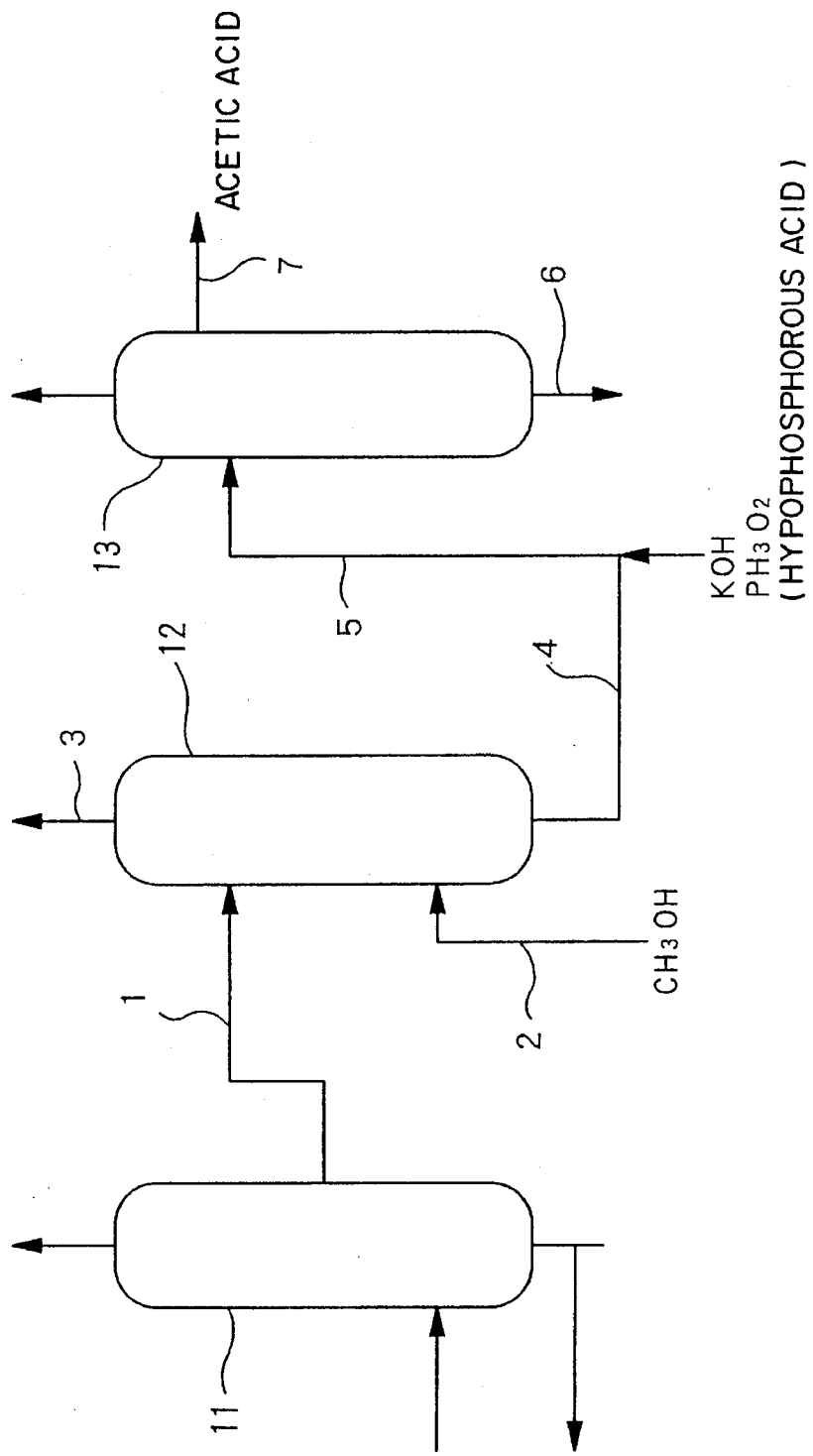

PROCESS FOR PREPARING ORGANIC CARBOXYLIC ACID

BACKGROUND OF THE INVENTION

The present invention relates to a process for preparing an organic carboxylic acid comprising conducting carbonylation reaction of alcohol using a rhodium catalyst and an iodide co-catalyst and separating an organic carboxylic acid from the reaction product. More particularly, the invention relates to a process for preparing an organic carboxylic acid having an extremely low content of iodide.

For preparing an organic carboxylic acid such as an acetic acid, there is conventionally known a process of reacting methanol with carbon monoxide in a reaction solvent in the presence of a rhodium carbonyl complex and methyl iodide. In this process, the reaction system needs a relatively high water content (about 15%). Therefore, a high energy is required for recovering the acetic acid and, what is more important, there is involved a drawback that an expensive material of high anticorrosion must be used for the apparatus because the iodide (specifically, hydrogen iodide (HI)) produced owing to the presence of a large amount of water is a highly material-corrosive substance. On that account, as an improved process of conducting the reaction in the presence of a small amount of water, a process comprising using an alkali metal salt in combination is disclosed in Japanese Patent Laid-Open Publication No. 298549/1987 (U.S. patent application Ser. No. 874734/1986), or a process comprising using a catalyst obtained by supporting a rhodium carbonyl complex on a vinylpyridine resin having a porous crosslinked structure is disclosed in Japanese Patent Laid-Open Publication No. 306253/1993 (U.S. Pat. No. 5,334,755).

In such processes for preparing an acetic acid as mentioned above, most of iodides such as methyl iodide used as the co-catalyst and hydrogen iodide produced as a by-product through hydrolysis of the methyl iodide are removed from the acetic acid by distillation, but the iodides still remaining must be necessarily removed. For example, according to the patent of Celanese Corp. (Japanese Patent Laid-Open Publication No. 246935/1993, i.e., U.S. patent application Ser. No. 799455/1991), the industrial standard with regard to the iodide content in the acetic acid is not more than 10 ppb. Particularly when the acetic acid is used as a material of vinyl acetate, the iodide content in the acetic acid is required to be not more than 1 ppb. The reason is that a gold or palladium catalyst used in the synthesis of vinyl acetate is prevented from deactivation caused by the iodide.

For removing iodides from the acetic acid obtained as above, a method of contacting the acetic acid with an alkali metal hydroxide or the like to remove iodides contained in the acetic acid is described in Japanese Patent Laid-Open Publication No. 55695/1982 (U.S. patent application Ser. No. 200553/1971), and a method of contacting the acetic acid with methanol to remove iodides contained in the acetic acid is described in Japanese Patent Laid-Open Publication No. 23016/1977 (U.S. patent application Ser. No. 603825/1975). Further, a method for removing iodides by contacting the acetic acid containing the iodides with a macro porus strong acid cation exchange resin in which silver or mercury is immobilized to a part of the active site is disclosed in Japanese Patent Publication No. 21031/1993 (U.S. patent application Ser. No. 708992/1985), or a method for removing iodides by contacting the acetic acid containing the iodides with a polymer resin to which a metallic salt capable of being precipitated by the reaction with an iodide is bonded in the form of coordination complex is disclosed in Japanese Patent Laid-Open Publication No. 246935/1993 (U.S. patent application Ser. No. 799455/1991).

In the above method of contacting the acetic acid with an alkali metal hydroxide or methanol to remove the iodides in the acetic acid, however, there is involved a problem on the removal of alkyl iodides, though the hydrogen iodide can be removed. That is, the effect of removing alkyl iodides, e.g., methyl iodide used as the co-catalyst, is small and the whole iodine content in the acetic acid is only reduced to several tens ppb at the lowest, so that the aforesaid standard of not more than 1 ppb cannot be attained.

On the other hand, the method of using a specific ion exchange resin to which silver or mercury is bonded described in Japanese Patent Publication No. 21031/1993 and the method of using a polymer resin having a metallic salt described in Japanese Patent Laid-Open Publication No. 246935/1993 are both intended to remove hexyl iodide mainly. That is, the methods for removing iodides disclosed in Japanese Patent Publication No. 21031/1993 and Japanese Patent Laid-Open Publication No. 246935/1993 are intended to remove hardly-separated hexyl iodide having been produced as a by-product in the acetic acid of a low water content which is obtained by adding an alkali metal salt such as LiI or NaI to the reaction system. By these methods, in addition to the removal of hexyl iodide, the total content of other alkyl iodide than hexyl iodide such as methyl iodide and hydrogen iodide can be reduced to not more than 1 ppb. However, the specific resins used in these methods are high in the production cost. Moreover, if the removing methods are applied to the preparation of an acetic acid, a problem of increase of cost for preparing an acetic acid takes place, because silver or mercury must be recovered. Accordingly, a process for easily and economically preparing an organic carboxylic acid such as an acetic acid having an iodide content of not more than 1 ppb has been eagerly desired.

SUMMARY OF THE INVENTION

It is an object of the present invention to provide a process for preparing an organic carboxylic acid having an extremely low content of iodide. The present inventors have found that in the process for preparing an acetic acid using a catalyst obtained by supporting a rhodium carbonyl complex on a vinylpyridine resin having a porous structure disclosed in the aforesaid Japanese Patent Laid-Open Publication No. 306253/1993 and not using an alkali metal iodide in the reaction system, if an alkyl iodide containing an alkyl group of 1 to 5 carbon atoms is used as a co-catalyst and the reaction is continued until a water content in the reaction product becomes low, hexyl iodide is never produced in the reaction product. On the other hand, the present inventors have studied on a method for removing iodides by treating an organic carboxylic acid containing an alkyl iodide with a resin, and as a result, they have found that an insoluble resin containing a pyridine ring in its resin structure can efficiently remove an alkyl iodide containing an alkyl group of 1 to 5 carbon atoms without modifying the resin with silver or mercury.

If an acetic acid is separated from the reaction product obtained by the process found by the present inventors and the acetic acid is treated with the insoluble resin, an acetic acid having an extremely low iodide content can be economically prepared. Based on this fact, the present invention described below has been accomplished.

That is, the process for preparing an organic carboxylic acid according to the invention comprises a production step in which alcohol is reacted with carbon monoxide in a reaction solvent in the presence of a rhodium-containing solid catalyst obtained by immobilizing rhodium in an insoluble carrier (I) containing a pyridine ring in its resin structure and an alkyl iodide containing an alkyl group of 1 to 5 carbon atoms, to obtain a reaction product having a water content of 0.5 to 10% by weight; and a removing step in which an organic carboxylic acid is separated and recovered from the reaction product, and the recovered organic carboxylic acid is contacted with an insoluble carrier (II) containing a pyridine ring in its resin structure, to remove an iodide contained in the organic carboxylic acid.

According to the present invention described above, the organic carboxylic acid having a water content of 0.5 to 10% by weight which is obtained by the production step of reacting alcohol with carbon monoxide in a reaction solvent in the presence of a rhodium-containing solid catalyst obtained by immobilizing rhodium in an insoluble carrier (I) containing a pyridine ring in its resin structure and an alkyl iodide containing an alkyl group of 1 to 5 carbon atoms, or its purified product is brought into contact with an insoluble carrier (II) containing a pyridine ring in its resin structure. As a result, the iodide contained in the organic carboxylic acid or its purified product is reacted with the pyridine ring of the insoluble carrier (II) and is fixed. Hence, the iodide such as an alkyl iodide can be removed from the organic carboxylic acid with high efficiency, and thereby an organic carboxylic acid having an extremely low iodide content can be prepared. In the present invention, moreover, the insoluble carrier (II) used in the removing step is lower in the production cost as compared with the ion exchang resin containing silver or mercury, and the disposal of the insoluble carrier (II) having iodide fixed therein is very easy because recovery of silver or mercury is unnecessary.

BRIEF DESCRIPTION OF THE DRAWING

FIG. 1 is a flow chart showing a purification process of an organic carboxylic acid capable of being incorporated into the process for preparing an organic carboxylic acid according to the present invention.

DESCRIPTION OF PREFERRED EMBODIMENT OF THE INVENTION

The process for preparing an organic carboxylic acid according to the invention comprises a production step to produce an organic carboxylic acid and a removing step to remove an iodide.

First, the insoluble carrier (I) used for the rhodium-containing solid catalyst which is used in the production step of an organic carboxylic acid in the invention is an insoluble resin containing a pyridine ring in its resin structure, and has a crosslinking degree of 30 to 60%, preferably 35 to 60%, a pore volume of 0.2 to 0.4 cc/g, preferably 0.3 to 0.4 cc/g, and a mean pore diameter of 20 to 100 nm, preferably 30 to 90 nm. The insoluble carrier having a crosslinking degree of less than 30% is unfavorable, because dissociation of pyridine ring from its resin structure increases and abrasion resistance lowers when the insoluble carrier is used for the rhodium-containing solid catalyst. The insoluble carrier having a crosslinking degree of more than 60% is also unfavorable, because reduction of catalytic activity takes place. The insoluble carrier (I) having a pore volume of less than 0.2 cc/g is unfavorable, because reduction of catalytic activity takes place when the insoluble carrier is used for the rhodium-containing solid catalyst. On the other hand, the insoluble carrier having a pore volume of more than 0.4 cc/g is also unfavorable, because a problem of lowering of abrasion resistance takes place. The insoluble carrier having a mean pore diameter of less than 20 nm is unfavorable, because reduction of catalytic activity takes place when the insoluble carrier is used for the rhodium-containing solid catalyst. On the other hand, the insoluble carrier having a mean pore diameter of more than 100 nm is also unfavorable, because a problem of lowering of abrasion resistance takes place.

The insoluble carrier (I) containing a pyridine ring in its resin structure can be obtained by, for example, reacting vinylpyridine with a divinyl monomer as a crosslinking agent, or reacting vinylpyridine with a vinyl monomer including a divinyl monomer. Particular examples of the pyridine ring-containing insoluble carrier (I) include a 4-vinylpyridine-divinylbenzene copolymer, a 2-vinylpyridine-divinylbenzene copolymer, a styrene-vinylpyridine-divinylbenzene copolymer, a vinylmethylpyridine-divinylbenzene copolymer and a vinylpyridine-methyl acrylate-ethyl diacrylate copolymer. Such copolymers can be obtained by copolymerization methods conventionally known, e.g., a precipitant addition method, a linear polymer addition method, a swelling agent/precipitant addition method and a diluent/linear polymer addition method.

For preparing the pyridine ring-containing insoluble carrier (I), for example, a process disclosed in Japanese Patent Publication No. 2573/1986 (Japanese Patent Laid-Open Publication No. 10680/1978) can be used. According to this process, the pyridine tin g-containing insoluble carrier (I) is prepared by subjecting a mixture of a vinylpyridine monomer, a crosslinking agent having two vinyl groups and if necessary a vinyl monomer to polymerization reaction in the presence of a radical polymerization reaction catalyst. In this case, an aqueous suspension polymerization using water as a medium is adopted as the polymerization reaction. Further, a suspension stabilizer and a precipitant are added to the polymerization reaction system. Examples of the suspension stabilizers used herein include water-soluble high molecular compounds such as polyvinyl alcohol, hydroxyethyl cellulose, carboxylmethyl cellulose, sodium polymethacrylate, sodium polyacrylate, starch, gelatin and a styrene-maleic anhydride copolymer; and inorganic salts such as calcium carbonate, calcium sulfate, bentonite and magnesium silicate. To the reaction system, sodium chloride, sodium sulfite, etc. may be also added. Examples of the precipitants used herein include organic solvents which act as solvents on monomers but act as poor solvents on the produced polymer, such as hydrocarbons of 5 to 10 carbon atoms (e.g., isooctane), alcohols and esters. In the preparation of the pyridine ring-containing insoluble carrier (I), the crosslinking degree of the resulting pyridine ring-containing insoluble resin can be controlled by the amount of the crosslinking agent. The pore volume and the mean pore diameter thereof can be mainly controlled by the kind and the amount of the precipitant, and can be further controlled by the kind and the amount of the suspension stabilizer and the reaction temperature.

Examples of the vinylpyridine monomers used for obtaining the pyridine ring-containing insoluble carrier (I) include 4-vinylpyridine, 2-vinylpyridine, a 4-vinylpyridine derivative having a lower alkyl group such as methyl or ethyl on the pyridine ring and a 2-vinylpyridine derivative having such lower alkyl group on the pyridine ring. To the vinylpyridine monomers may be added other vinyl monomers, e.g., aromatic vinyl monomers such as styrene and vinyltoluene. The amount of the aromatic vinyl monomer added is desirably not more than 30% by mol, preferably not more than 20% by mol, based on the total amount of all monomers.

Examples of the crosslinking agents having two vinyl groups and copolymerized with the vinylpyridine monomer include aromatic compounds such as divinylbenzene and divinyltoluene, and aliphatic compounds such as butadiene. The amount of the crosslinking agent can be properly determined according to the preset crosslinking degree of the pyridine ring-containing insoluble resin.

The crosslinking degree of the insoluble carrier (I) in the invention is defined as follows.

[Crosslinking degree]

Crosslinking degree $(\%) = A/B \times 100$ wherein A is a weight of the crosslinking agent contained in the resin, and B is a weight of the vinylpyridine monomer contained in the resin.

The pore volume and the mean pore diameter of the insoluble carrier are measured and calculated as follows.

[Pore volume]

The pore volume is measured by a mercury penetration method. In this mercury penetration method, the pore volume is measured under the conditions of a mercury surface tension of 474 dyne/cm at 25° C. and a contact angle of 140 degrees with varying the absolute mercury pressure from 1 to 200 kg/cm$^2$-G.

[Mean pore diameter]

The mean pore diameter is calculated from the pore volume measured as above and the surface area of the insoluble resin measured by the B.E.T. method in accordance with the following equation:

Mean pore diameter $(nm) = 4(C/D) \times 10^3$ wherein C is a pore volume (cc/g) of the resin, and D is a surface area (m$^2$/g) of the resin.

The insoluble carrier (I) is in the particulate form, preferably in the spherical form, and the particle diameter thereof is in the range of 0.01 to 4 mm, preferably 0.1 to 2 mm, more preferably 0.4 to 2 mm.

The rhodium supported on the insoluble carrier (I) is in the form of a rhodium carbonyl complex represented by, for example, $[Rh(CO)_2I_2]^-$. For supporting the rhodium carbonyl complex on the insoluble carrier (I), the following methods are employed.

(1) A method of supporting a rhodium ion on a nitrogen atom of the pyridine ring of the insoluble carrier (I) in an aqueous solution and then changing it into a rhodium carbonyl complex in an organic solvent in the presence of an alkyl iodide and carbon monoxide.

The reaction of the pyridine ring with rhodium in this method is represented by the following formulas. In general, the supporting of rhodium is carried out under the reaction conditions of ordinary temperature and ordinary pressure, and the changing to the rhodium carbonyl complex of the supported rhodium is carried out under the same reaction conditions as for the carbonylation of methanol described later.

Supporting of rhodium

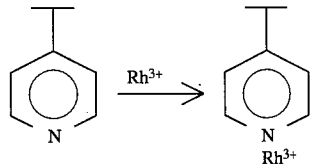

Complexing of supported rhodium

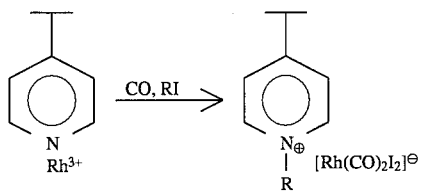

In the above formulas, R is a lower alkyl group.

(2) A method of contacting the insoluble carrier (I) with a rhodium salt in a solvent containing an alkyl iodide under a pressure of carbon monoxide.

In this method, the rhodium salt and the insoluble carrier (I) are generally contacted with each other under the carbonylation reaction conditions of methanol described later. The rhodium-containing solid catalyst thus obtained has such a structure that the rhodium carbonyl complex $[Rh(CO)_2I_2]^-$ produced by the reaction of the rhodium salt, the alkyl iodide and carbon monoxide is ion-bonded to a pyridinium salt obtained by quaternization of the pyridine ring contained in the insoluble carrier (I) by the alkyl iodide.

Examples of the rhodium salts include rhodium halides such as rhodium chloride, rhodium bromide and rhodium iodide. Examples of the alkyl iodides include those having lower alkyl groups of 1 to 5 carbon atoms, such as methyl iodide, ethyl iodide and propyl iodide. Of these, particularly preferably used is methyl iodide. The alkyl iodide is used in an amount of 2 to 2,000 mol, preferably 50 to 500 mol, based on 1 mol of the rhodium salt. The pressure of carbon monoxide for contacting the rhodium salt with the alkyl iodide is in the range of 7 to 30 kg/cm$^2$-G, preferably 10 to 20 kg/cm$^2$-G.

The amount of the supported rhodium carbonyl complex in the rhodium-containing solid catalyst used in the production step of an organic carboxylic acid in the invention is in the range of 0.2 to 2% by weight, preferably 0.5 to 1.0% by weight, in terms of rhodium, based on the amount of the insoluble carrier (I). If the amount of the supported rhodium carbonyl complex exceeds 2% by weight, the catalytic activity per 1 mol of the rhodium is reduced, thereby to lower the product yield per 1 mol of the rhodium (mol/mol-Rh/hr). Moreover, in the use of the rhodium-containing solid catalyst, the dissociation quantity of the rhodium carbonyl complex from the catalyst becomes large. Even if the amount of the rhodium-containing solid catalyst is increased, the concentration of rhodium dissociated from the catalyst and present in the reaction system does not vary so much, as far as the amount of the supported rhodium carbonyl complex is unchanged. In order to effectively use rhodium, therefore, it is preferred to use a rhodium-containing solid catalyst having a low content of the supported rhodium carbonyl complex in a large amount. However, if the amount of the supported rhodium carbonyl complex is less than 0.2% by weight, the amount of the catalyst necessary for obtaining a desired reaction rate becomes too large, and as a result, stirring in the reactor becomes difficult, or surface abrasion of the catalyst easily takes place.

Such a rhodium-containing solid catalyst as mentioned above is useful as a catalyst for preparing an acetic acid by means of carbonylation of methanol, and moreover, such catalyst can be generally used as a catalyst for the carbonylation reaction of lower alcohols.

Next, the production step of the organic carboxylic acid in the invention will be described in detail with reference to an embodiment of the process for preparing an acetic acid by means of carbonylation of methanol.

In the embodiment of the process for preparing an acetic acid, the rhodium-containing solid catalyst and an alkyl iodide having a lower alkyl group of 1 to 5 carbon atoms are allowed to exist in a reaction solvent. Then, into the reaction solvent are introduced methanol and carbon monoxide to react them so as to prepare an acetic acid. For the reaction, reactors of various types such as fixed bed type, stirred tank type and expanding bed type can be employed.

The amount of the rhodium-containing solid catalyst to be fed to the reactor may be generally in the range of 2 to 40% by weight based on the weight of the solution in the reactor, but in the case of a stirred tank reactor, the amount thereof is preferably in the range of about 2 to 25% by weight. In a fixed bed reactor, the amount thereof is preferably in the range of about 20 to 40% by weight, and in an expanding bed reactor, the amount thereof is preferably in the range of about 2 to 25% by weight.

As the reaction solvent, various ones conventionally known can be employed, but in general, organic solvents containing carbonyl groups of 2 or more carbon atoms are preferred. Examples of such reaction solvents include carboxylic acids such as acetic acid and methyl acetate and carboxylic esters. In the carbonylation reaction of methanol, a main reaction of the following reaction formula (1) and side reactions of the following reaction formulas (2) and (3) take place. The side reactions of the formulas (2) and (3) are reversing reactions, and if the amount of $CH_3OH$ in the reaction system is small, the reaction proceeds in such a manner that the amount of $H_2O$ decreases.

$$CH_3OH + CO \rightarrow CH_3COOH \quad (1)$$

$$CH_3COOH + CH_3OH \leftrightharpoons CH_3COOCH_3 + H_2O \quad (2)$$

$$2CH_3OH \leftrightharpoons CH_3OCH_3 + H_2O \quad (3)$$

The water content in the reaction solvent is in the range of 0.05 to 50% by weight, preferably about 0.1 to 20% by weight, more preferably 0.5 to 10% by weight. If the water content is less than the lower limit of the above range, the activity of the carbonylation reaction is reduced. On the other hand, if the water content exceeds the upper limit of the above range, the amount of the unsupported rhodium in the catalyst is increased and hydrogen iodide that is highly corrosive is produced in a large amount by the following reaction.

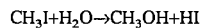
$$CH_3I + H_2O \rightarrow CH_3OH + HI$$

As the alkyl iodide to be contained in the reaction solvent, an alkyl iodide of 1 to 5 carbon atoms is used, and specifically, methyl iodide is preferably used.

The amount of the reaction solvent in the reactor is not less than 0.30 part by weight, preferably not less than 2.40 parts by weight, based on 1 part by weight of methanol. The amount of the reaction solvent in the reactor can be determined in the following manner according to the type of the reactor used. In a batch type reactor, the amount of the reaction solvent means an amount of the solvent to methanol in the starting solution fed to the reactor. Since the amount of methanol decreases with a progress of the reaction, the concentration of the reaction solvent in the reactor becomes higher than the concentration of the reaction solvent at the time the starting materials are initially fed.

In a continuous stirred tank reactor, since the solution in the reactor is uniformly mixed, the solution has substantially the same composition as that of a solution of the reaction product drawn out from the reactor outlet. That is, in this case, the amount of the solvent in the reactor is set substantially as an amount of the reaction solvent to the methanol in the reaction product drawn out from the reactor outlet.

In a piston flow reactor, the amount of the reaction solvent is set as an amount of the solvent to the methanol in the whole solution fed to the reactor. In this case, the concentration of methanol lowers according as the solution comes close to the reactor outlet from the reactor inlet, and the amount of the reaction solvent to the methanol increases according as the solution comes close to the reactor outlet. That is, the amount of the reaction solvent can be set as an amount of the solvent to methanol in the whole solution fed through the reactor inlet.

By keeping the amount of the reaction solvent in the reactor within the above range, the reaction activity of the rhodium carbonyl complex, namely, an active center of the catalyst, can be increased, and the bonding stability between the rhodium carbonyl complex and the pyridinium salt can be enhanced. In addition, dissociation of rhodium from the insoluble carrier can be effectively prevented so that the carbonylation reaction of methanol smoothly proceeds at a high reaction rate, and, what is more important, if the amount of the reaction solvent in the reactor is kept within the above range, the rhodium carbonyl complex is stably present even under the condition of an extremely low carbon monoxide partial pressure of 7 $kg/cm^2$-G, as described later. As a result, the carbonylation reaction of methanol can be made to proceed at a high reaction rate. This means that a special pressure-resistant container does not need to be used as a reactor, and therefore the reactor cost can be prominently reduced, and a useful and economical process for preparing an acetic acid can be obtained.

In the above-mentioned preparation of an acetic acid, the carbon monoxide partial pressure for carrying out the carbonylation reaction of methanol is not less than 7 $kg/cm^2$-G, preferably not less than 10 $kg/cm^2$-G. The upper limit of the carbon monoxide partial pressure is desirably about 30 $kg/cm^2$-G from the viewpoints of increase of reaction rate, reaction effect and economical effect. Accordingly, the carbon monoxide partial pressure can be set within the range of 7 to 30 $kg/cm^2$-G, preferably 10 to 20 $kg/cm^2$-G. By setting the carbon monoxide partial pressure within the above range, the total pressure for the reaction can be lowered to an economical level, in concrete, generally 10 to 60 $kg/cm^2$-G, preferably 15 to 40 $kg/cm^2$-G, more preferably 15 to 30 $kg/cm^2$-G.

The reaction temperature in the carbonylation reaction of methanol is in the range of 140° to 250° C., preferably 160° to 230° C., but the upper limit can be appropriately determined according to heat resistance of the insoluble carrier (I) used for the rhodium-containing solid catalyst. The amount of the alkyl iodide present in the reaction system is in the range of 1 to 40% by weight, preferably 5 to 30% by weight, based on the weight of the solution in the reactor. The rhodium concentration in the reaction system is not less than 50 ppm by weight, preferably not less than 300 ppm by weight, more preferably not less than 400 ppm by weight, based on the weight of the solution in the reactor. The term "rhodium concentration" used herein means a proportion of the amount of rhodium to the amount of the solution in the reactor except the insoluble carrier (I).

In the above description of the production step, preparation of an acetic acid using an alcohol (starting material) and methanol is taken as an embodiment of the invention. However, in the process for preparing an organic carboxylic acid according to the invention, various combinations of alcohols (starting materials) and the resulting organic carboxylic acids can be mentioned, and some examples thereof are described below.

Ethanol→Propionic acid
Isopropanol→Isobutyric acid
tert-Butyl alcohol→Pivalic acid
Heptanol→Octanoic acid
Butanediol→Adipic acid
Phenol→Benzoic acid In the process for preparing an organic carboxylic acid according to the invention, the water content in the reaction product obtained by the above-mentioned production step of an organic carboxylic acid is made to be in the range of 0.5 to 10 % by weight. The term "reaction product" used herein means a reaction product at the time of completion of reaction in the case of a batch type reactor, and means a reaction product drawn out from the reactor outlet in the case of a continuous stirred tank reactor or a piston flow reactor.

In the production step of an organic carboxylic acid as mentioned above, the reactions of the aforesaid formulas (1), (2) and (3) are carried out, and in each of the reactions, the water content increases according as the reaction proceeds, because the beginning of the reaction is rich in methanol. However, as according as the methanol is consumed and the amount thereof is reduced, the reactions of the formulas (2) and (3) proceed in the left direction, so that the water content decreases. In the batch type reactor, therefore, the reaction is continued until the water content in the reaction product decreases with reduction of methanol so as to be not less than 10% by weight. Also in other kind of reactors, the water content in the reaction product drawn out can be adjusted within the range of 0.5 to 10% by weight by controlling the residence time of methanol in the reactor.

The reaction product containing an organic carboxylic acid produced by the production step under the above-described various conditions is characterized by low corrosiveness with hydrogen iodide and containing no hexyl iodide.

From the reaction product, the organic carboxylic acid is separated by a known method such as distillation. Then, in the removing step, the organic carboxylic acid is contacted with an insoluble carrier (II) containing a pyridine ring in its resin structure to remove an iodide, thereby to purify the organic carboxylic acid. For decreasing the iodide content to not more than 1 ppb, the organic carboxylic acid is preferably subjected to the following purification step to preliminarily decrease the iodide content to several tens ppb, prior to the contact with the insoluble carrier (II) in the removing step.

In the purification step, as shown in the process flow of FIG. 1, the organic carboxylic acid recovered from the first distillation column (light end column) 11 and containing an iodide in a high concentration (containing, for example, hydrogen iodide in an amount of about 1,000 ppm) is introduced into the upper part of the second distillation column (drying column) 12 through a line 1, while excess methanol is introduced into the lower part of the drying column 12 through a line 2. As a result, hydrogen iodide turns into methyl iodide according to the following reaction, and the methyl iodide thus produced is removed together with water from the top of the drying column 12 through a line 3.

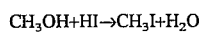

On the other hand, an organic carboxylic acid in which the hydrogen iodide content is decreased to about 100 ppb is obtained from the bottom of the drying column 12 through a line 4. Then, a mixture of this organic carboxylic acid and either an alkali metal hydroxide, an alkali metal salt or a mixture of said hydroxide or said salt with a hypophosphorous acid is introduced into the intermediate part of the third distillation column (heavy end column) 13 through a line 5. As a result, the hydrogen iodide turns into an alkali metal iodide (potassium chloride in the following example) according to the following reaction, and the alkali metal iodide thus produced is removed out from the bottom of the heavy end column 13 through a line while an organic carboxylic acid in which the hydrogen iodide content is decreased to about several ppb can be obtained from the top of the heavy end column 13 through a line 7.

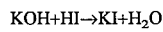

In the purification step stated above, the hydrogen halide is mainly removed, and the total amount of all iodides including alkyl halide and halogen in the organic carboxylic acid after the completion of the purification step is about several tens ppb.

In the process for preparing an organic carboxylic acid according to the invention, a step of contacting the organic carboxylic acid with active carbon to remove halogen contained in the organic carboxylic acid by means of adsorption may be carried out before and/or after the removing step in which the organic carboxylic acid is contacted with the insoluble carrier (II).

Next, the removing step in the process for preparing an organic carboxylic acid according to the invention will be described.

In this removing step, the organic carboxylic acid having been separated and/or purified as above is contacted with an insoluble carrier (II) containing a pyridine ring in its resin structure.

The insoluble carrier (II) preferably has a crosslinking degree of 10 to 70%. The insoluble carrier (II) having a crosslinking degree of less than 10% is unfavorable, because the resin structure easily undergoes swelling or shrinkage owing to the organic carboxylic acid. On the other hand, it is difficult to prepare an insoluble carrier having a crosslinking degree of more than 70%.

Such insoluble carrier can be obtained in a manner similar to that for the insoluble carrier (I) used for the rhodium-containing solid catalyst, and hence description thereof is omitted here.

In the removing step, the contact of the organic carboxylic acid containing an iodide with the insoluble carrier (II) is carried out by any of a method of feeding the organic carboxylic acid to the column charged with the insoluble carrier (II) (fixed bed), a method of contacting the organic carboxylic acid with the insoluble carrier (II) in the fluid state (fluidized bed, stirred tank), etc.

The temperature in the contact of the organic carboxylic acid containing an iodide with the insoluble carrier (II) is in the range of preferably 40° to 200° C., more preferably 70° to 180° C. If the contact temperature is lower than 40° C., the reaction between the pyridine ring and the iodide described later is insufficiently made, whereby the iodide removal efficiency is lowered. Since the pyridine ring-containing insoluble resin is decomposed at a temperature higher than 200° C., the contact temperature is required to be not higher than 200° C.

When the organic carboxylic acid containing an iodide is contacted with the insoluble carrier (II) as described above, the pyridine ring in the insoluble carrier (II) is quaternized by the iodide in accordance with the following formula.

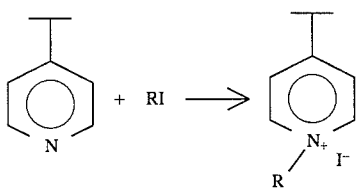

With the quaternization of the pyridine ring, the iodide is reacted with the pyridine ring and fixed in the insoluble carrier (II), whereby the iodide is removed from the organic carboxylic acid.

According to the process for preparing an organic carboxylic acid of the invention, the alkyl iodide used as a co-catalyst in the aforesaid production step, particularly methyl iodide, and hydrogen iodide produced as a by-product by hydrolysis of methyl iodide can be fixed in the insoluble carrier (II) and removed. As is apparent from the examples described later, a removal rate of not less than 95% can be easily attained, though the removal rate varies according to the temperature, the initial concentration of methyl iodide, etc. If the initial concentration of methyl iodide is not more than several tens ppb, the iodide content in the organic carboxylic acid after the removing step becomes not more than 1 ppb. However, if hexyl iodide is contained in the organic carboxylic acid, it is impossible to effectively remove the hexyl iodide in the removing step of the invention. Accordingly, in the production step of the invention, it is important to produce an organic carboxylic acid not including alkyl iodide of 6 or more carbon atoms.

The insoluble carrier (II) used in the invention does not contain any metal such as mercury or silver, so that the production cost of the carrier can be lowered. Moreover, since recovery of mercury or silver is unnecessary, the disposal procedure of the insoluble carrier (II) having the iodide fixed therein can be simplified and the disposal cost can be prominently reduced.

In the present invention, the insoluble carrier (II) in which the iodide has been fixed can be used as the insoluble carrier (I) of the rhodium-containing solid catalyst used in the aforesaid step for producing an organic carboxylic acid having a low water content, and thereby effectual use of resources and reduction of production cost of an organic carboxylic acid become possible. If an insoluble carrier having a crosslinking degree of 30 to 60%, preferably 35 to 60%, a pore volume of 0.2 to 0.4 cc/g, preferably 0.3 to 0.4 cc/g, and a mean pore diameter of 20 to 100 nm, preferably 30 to 90 nm, is used as the insoluble carrier (II) containing a pyridine ring in its resin structure, it becomes easy to use the insoluble carrier (II) as the insoluble carrier (I).

The present invention will be further described with reference to the following examples.

EXAMPLE 1

[Preparation of an acetic acid of a low water content using a homogeneous catalyst]

Into a titanium autoclave (250 cc) were introduced 14 g of methanol, 14 g of methyl iodide, 112 g of an acetic acid and 0.14 g of rhodium chloride trihydrate ($RhCl_3 \cdot 3H_2O$). After the autoclave was purged twice with nitrogen under a pressure of 50 kg/cm$^2$, the content in the autoclave was heated to 180° C. with stirring at a stirring rate of 1,400 rpm. Then, carbonmonoxide is fed to the autoclave through a pressure control valve so that the total pressure became 50 kg/cm$^2$, to perform reaction. In this procedure, the carbon monoxide was fed from a reserve tank (0.6 liter) having a pressure of 70 kg/cm$^2$, and from the reduction in the pressure of the reserve tank, a consumption rate of the carbon monoxide was sought. This consumption rate was taken as the reaction rate.

The reaction was carried out for 35 minutes after feeding of carbon monoxide. The reaction rate per solution volume was 1.3 mol/liter/hr, and the reaction rate per hour–per Rh mol was 320 mol/mol-Rh/hr. Thereafter, the reactor was rapidly cooled and purged twice with nitrogen under a pressure of 50 kg/cm$^2$, followed by recovering the reaction product. The reaction product was measured on the composition and the iodine ion concentration. The results are set forth in Table 1.

EXAMPLE 2

[Preparation of an acetic acid of a low water content using a heterogeneous catalyst]

First, a rhodium-containing solid catalyst was prepared in the following manner. In methanol was immersed 10.5 g (dry weight: 6.7 g) of a 4-vinylpyridine-divinylbenzene copolymer resin (insoluble carrier (I)) having a crosslinking degree of 60%, a pore volume of 0.32 cc/g, a mean pore diameter of 21 nm and a mean particle diameter of 0.43 mm for a sufficient time. Then, to the copolymer resin was added 140 g of a mixed solution of methyl iodide, methanol and an acetic acid (methyl iodide: 8% by weight, methanol: 45% by weight, acetic acid: 47% by weight). The resulting mixture was introduced into a titanium autoclave (250 cc), and thereto was further added 0.14 g of rhodium chloride trihydrate ($RhCl_3 \cdot 3H_2O$). The autoclave was purged two times with nitrogen under a pressure of 50 kg/cm$^2$ and was then heated. At the time the temperature of the mixture reached 190° C., carbon monoxide is fed to the autoclave through a pressure control valve so that the total pressure became 50 kg/cm$^2$ (initial partial pressure of carbon monoxide: 15 kg/cm$^2$). After 30 minutes, the reactor was cooled and purged with nitrogen. Then, the reaction product was recovered by decantation and prepared catalyst was washed several times with methanol. Rh in the reaction product was analyzed by atomic absorption spectrometry, and methyl iodide in the reaction product was analyzed by gas chromatography. As a result, it was confirmed that Rh corresponding to 0.8% by weight based on the resin weight and iodine of equivalent amount corresponding to most of the pyridine rings were fixed.

Subsequently, the procedures of example 1 were repeated except that the rhodium-containing solid catalyst prepared above was used in place of the rhodium chloride trihydrate ($RhCl_3 \cdot 3H_2O$) and that methanol, methyl iodide, water and the acetic acid were added in amounts of 28 g, 14 g, 0 g and 98 g, respectively, to perform reaction. The reaction product was recovered, and measured on the composition and the iodine ion concentration. The results are set forth in Table 1.

Further, the reaction rate in the above reaction was measured. As a result, the reaction rate per solution volume was 4.3 mol/liter/hr, and the reaction rate per hour·per Rh mol was 1,070 mol/mol-Rh/hr. As is apparent from the comparison between the results on these reaction rates and the results on the reaction rates of Example 1, use of the rhodium-containing solid catalyst is more advantageous than use of the homogeneous catalyst in the preparation of an acetic acid having a low water content.

Furthermore, a continuous flow test was carried out. In this test, a mixture of methanol (20% by weight), methyl iodide (10% by weight) and an acetic acid (70% by weight)

was fed to an reactor equipped with a stirrer and holding therein the above-prepared rhodium-containing solid catalyst under the conditions of a temperature of 180° C., a pressure of 50 kg/cm²-G and a residence time of 35 minutes, while carbon monoxide was fed to the reactor in an amount enough to maintain the total reaction pressure. As a result, the same results as mentioned above were obtained.

EXAMPLE 3

[Preparation of an acetic acid of a high water content using hexane as a starting material and using a homogeneous catalyst]

The procedures of example 1 were repeated except that 14 g of methanol, 14 g of methyl iodide, 21 g of water, 91 g of an acetic acid, 0.14 g of rhodium chloride trihydrate ($RhCl_3 \cdot 3H_2O$) and 1.4 g of hexane were added to the titanium autoclave (250 cc), to perform reaction. The reaction product was recovered, and measured on the composition and the iodine ion concentration. The results are set forth in Table 1. It was confirmed that the reaction product contained no hexyl iodide.

Further, the reaction rate in the above reaction was measured. As a result, the reaction rate per solution volume was 4.4 mol/liter/hr, and the reaction rate per hour•per Rh mol was 1,090 mol/mol-Rh/hr.

EXAMPLE 4

[Preparation of an acetic acid of a low water content using lithium iodide and hexane as starting materials and using a homogeneous catalyst]

The procedures of example 1 were repeated except that 14 g of methanol, 14 g of methyl iodide, 7 g of water, 105 g of an acetic acid, 0.14 g of rhodium chloride trihydrate ($RhCl_3 3H_2O$), 21 g of lithium iodide (LiI) and 1.4 g of hexane were added to the titanium autoclave (250 cc), to perform reaction. The reaction product was recovered, and measured on the composition and the iodine ion concentration. The results are set forth in Table 1. It was confirmed that the reaction product contained 6.2 ppm of hexyl iodide.

Further, the reaction rate in the above reaction was measured. As a result, the reaction rate per solution volume was 4.6 mol/liter/hr, and the reaction rate per hour•per Rh mol was 1,140 mol/mol-Rh/hr.

EXAMPLE 5

[Preparation of an acetic acid of a low water content using hexane as a starting material and using a heterogeneous catalyst]

The procedures of Example 2 were repeated except that 1.4 g of hexane was added to the reaction system, to perform reaction. The reaction product was recovered, and measured on the composition and the iodine ion concentration. The results are set forth in Table 1. It was confirmed that the reaction product contained no hexyl iodide.

Further, the reaction rate in the above reaction was measured. As a result, the reaction rate per solution volume was 4.3 mol/liter/hr, and the reaction rate per hour•per Rh mol was 1,070 mol/mol-Rh/hr.

TABLE 1

|  | Ex. 1 | Ex. 2 | Ex. 3 | Ex. 4 | Ex. 5 |
|---|---|---|---|---|---|
| Temperature (°C.) | 180 | 180 | 180 | 180 | 180 |
| Pressure (kg/cm²) | 50 | 50 | 50 | 50 | 50 |

TABLE 1-continued

|  | Ex. 1 | Ex. 2 | Ex. 3 | Ex. 4 | Ex. 5 |
|---|---|---|---|---|---|
| [Starting material] | | | | | |
| Methanol (wt %) | 10 | 20 | 10 | 10 | 20 |
| Methyl iodide (wt %) | 10 | 10 | 10 | 10 | 10 |
| Water (wt %) | 0 | 0 | 15 | 5 | 0 |
| Acetic acid (wt %) | 80 | 70 | 65 | 75 | 70 |
| Total weight of starting materials (g) | 140 | 140 | 140 | 140 | 140 |
| Rhodium chloride trihydrate (g)* | 0.14 (400 ppm) | 0.14 (400 ppm) | 0.14 (400 ppm) | 0.14 (400 ppm) | 0.14 (400 ppm) |
| Amount of lithium iodide (g) | — | — | — | 21 | — |
| Amount of hexane (g) | — | — | 1.4 | 1.4 | 1.4 |
| [Reaction product] | | | | | |
| Methanol (wt %) | 0.3 | 0.6 | 0.1 | 0.5 | 0.6 |
| Methyl iodide (wt %) | 7.8 | 7.2 | 6.1 | 6.9 | 7.2 |
| Water (wt %) | 3.8 | 4.8 | 13.6 | 5.4 | 4.8 |
| Acetic acid (wt %) | 72.6 | 66.1 | 77.7 | 84.3 | 66.1 |
| Methyl acetate (wt %) | 15.5 | 21.3 | 2.4 | 3.0 | 21.3 |
| Dimethyl ether (wt %) | 0.1 | 0.1 | 0 | 0 | 0.1 |
| Hexyl iodide (ppm) | 0 | 0 | 0 | 6 | |
| Iodine ion concentration (ppm) | 110 | 400 | 5080 | 120000 | 406 |

*: The amount of rhodium chloride trihydrate means an amount of a rhodium chloride added to the starting materials or an amount of rhodium chloride supported on the insoluble resin carrier(I) used. Eeah value in parentheses means an amount of rhodium chloride to the total amount of the starting materials.

As shown in Table 1, in each of Example 2 and Example 5 wherein the reaction was carried out using the rhodium-containing solid catalyst, the reaction product had a sufficiently low water content of not more than 5% by weight.

In Example 4 wherein an acetic acid having a low water content was obtained, hexane and lithium iodide were added as starting materials, and hence hexyl iodide was contained in the reaction product, while in Example 5, no hexyl iodide was observed in the reaction product in spite that hexane was added as a starting material. It is also apparent that the iodine ion concentration in Example 3 wherein the reaction product had a high water content was extremely higher than that in Example 5.

EXAMPLES 6–11

Comparative Example 1

A 4-vinylpyridine-divinylbenzene copolymer resin (insoluble carrier (II), dry weight: 2.5 g) having a crosslinking degree of 39%, a pore volume of 0.317 cc/g, a mean pore diameter of 80.8 nm and a mean particle diameter of 0.4 mm was sufficiently swelled in an acetic acid, then charged in a glass column (10 mm (diameter)×100 mm (length)), and kept at a constant temperature in a constant temperature water bath. To the column, an acetic acid (special grade) having been added with methyl iodide or hexyl iodide was continuously fed in a rising current under the conditions set forth in Table 2. The iodide concentration in the effluent was measured by ICP analysis. The result is set forth in Table 2.

TABLE 2

|  | Ex. 6 | Ex. 7 | Ex. 8 | Ex. 9 | Ex. 10 | Ex. 11 | Comp. Ex. 1 |
|---|---|---|---|---|---|---|---|
| Column Temperature (°C.) | 42 | 50 | 80 | 80 | 80 | 80 | 35 |
| Charge weight (g on dry basis) | 2.5 | 2.5 | 2.5 | 2.5 | 2.5 | 2.5 | 2.5 |
| Flow rate (ml/hr) | 27 | 27 | 27 | 27 | 19.4 | 27 | 27 |
| Residence time (min) | 17.4 | 17.4 | 17.4 | 17.4 | 24 | 17.4 | 17.4 |
| Concentration of methyl iodide (starting material) (ppm) | 520 | 520 | 520 | 10 | 0.10 | — | 520 |
| Concentration of hexyl iodide (starting material) (ppm) | — | — | — | — | — | 620 | — |
| Iodide concentration (reactor outlet) (ppm) | 250 | 156 | 26 | 0.5 | <0.001 | 570 | 406 |
| Testing time (min) | 180 | 60 | 60 | 60 | 60 | 60 | 180 |
| Methyl iodide removal rate (%) | 52 | 70 | 95 | 95 | >99 | — | 22 |
| Hexyl iodide removal rate (%) | — | — | — | — | — | 8.1 | — |

Comparative Example 2

The procedures of Example 10 were repeated except that a 4-vinylpyridine-divinylbenzene copolymer resin having a crosslinking degree of 2% was used as the insoluble carrier (II), to remove methyl iodide in the acetic acid. The iodide concentration in the effluent was measured by ICP analysis. The result is set forth in Table 3.

EXAMPLE 12

The procedures of Example 10 were repeated except that a 4-vinylpyridine-divinylbenzene copolymer resin having a crosslinking degree of 60%, a pore volume of 0.267 cc/g, a mean pore diameter of 33.4 nm and a mean particle diameter of 0.4 mm was used as the insoluble carrier (II), to remove methyl iodide in the acetic acid. The iodide concentration in the effluent was measured by ICP analysis. The result is set forth in Table 3.

Comparative Example 3

The procedures of Example 10 were repeated except that a 4-vinylpyridine-divinylbenzene copolymer resin having a crosslinking degree of 75%, a pore volume of 0.215 cc/g, a mean pore diameter of 24.2 nm and a mean particle diameter of 0.35 mm was used as the insoluble carrier (II), to remove methyl iodide in the acetic acid. The iodide concentration in the effluent was measured by ICP analysis. The result is set forth in Table 3.

TABLE 3

|  | Comp. Ex. 2 | Ex. 12 | Comp. Ex. 3 |
|---|---|---|---|
| Column temperature (°C.) | 80 | 80 | 80 |
| Charge weight (g on dry basis) | 2.5 | 2.5 | 2.5 |
| Crosslinking degree (%) | 2 | 60 | 75 |
| Flow rate (ml/hr) | 19.4 | 19.4 | 19.4 |
| Residence time (min) | 24 | 24 | 24 |
| Concentration of methyl iodide (starting material) (ppm) | 0.10 | 0.10 | 0.10 |
| Iodide concentration (reactor outlet) (ppm) | 0.03 | <0.001 | 0.03 |
| Testing time (min) | 60 | 60 | 60 |
| Methyl iodide removal rate (%) | 70 | >99 | 70 |

As is apparent from the results set forth in Table 2, in Examples 6 to 11 wherein the column temperature was not lower than 40° C., the methyl iodide removal rate was sufficiently high and not less than 50%, but in Comparative Example 1 wherein the column temperature was lower than 40° C., the methyl iodide removal rate was markedly lowered. Further, as is apparent from the results set forth in Table 2 and Table 3, the removal of iodide owing to the insoluble carrier (II) in the removing step of the process for preparing an organic carboxylic acid according to the invention was not effective for hexyl iodide contained in the organic carboxylic acid, but methyl iodide in the acetic acid was able to be removed at an extremely high removal rate. Moreover, it is also apparent that the crosslinking degree of the insoluble carrier (II) is preferably in the range of 10 to 70%.

As shown in Example 5, it is supposable that an organic carboxylic acid having an iodide content of not more than 1 ppb can be prepared if the organic carboxylic acid separated from the reaction product obtained in the production step of the invention not accompanied by production of hexyl iodide is subjected to the iodide removing step of the invention, and this was ascertained by the following examples.

EXAMPLE 13

The crude acetic acid obtained in the production step of an acetic acid in Example 2 was introduced into the second tray from the bottom of a low boiling column having ten trays and operated at 125° C. under 3 kg/cm². Then, 1,000 g of the acetic acid recovered from the fifth tray from the bottom of the low boiling column and 17 g of methanol were introduced into the twenty first tray and the sixth tray from the bottom, respectively, of a dehydration column having 34 trays and operated at a column top temperature of 133° C. under a column top pressure of 4.5 kg/cm². Thereafter, to the reaction solution recovered from the bottom of the dehydration column were added a 50 wt. % hypophosphorous acid aqueous solution and a 50 wt. % potassium hydroxide aqueous solution in amounts of 0.002% by weight and 0.02% by weight, respectively. The resulting mixture was introduced into the fourteenth tray from the bottom of a high boiling column having 50 trays and operated at 120° C. under atmospheric pressure, and the reaction solution was recovered from the upper part of the high boiling column. The iodide concentration in the reaction solution thus recovered was 20 ppb.

Subsequently, the reaction solution was processed in the same manner as described in Example 10 to remove iodide. As a result, the iodide concentration in the acetic acid thus processed was 0.5 to 1 ppb. From this fact, it has been confirmed that an organic carboxylic acid having an iodide content of not more than 1 ppb can be prepared by separating an organic carboxylic acid from the reaction product obtained in the production step of the invention stated in Example 2 and Example 5 and then subjecting the organic carboxylic acid to the iodide removing step of the invention.

EXAMPLE 14

The procedures of Example 2 were repeated except that a 4-vinylpyridine-divinylbenzene copolymer resin having a crosslinking degree of 39%, a pore volume of 0.317 cc/g, a mean pore diameter of 80.8 nm and a mean particle diameter of 0.4 mm was used as a 4-vinylpyridine-divinylbenzene copolymer resin (insoluble carrier (I)), to produce an acetic acid. Then, the crude acetic acid thus obtained was processed in the same manner as described in Example 10 to remove iodide. As a result, the iodide concentration in the acetic acid thus processed was 0.5 to 1 ppb. From this fact, it has been confirmed that an organic carboxylic acid having an iodide content of not more than 1 ppb can be prepared by separating an organic carboxylic acid from the reaction product obtained in the production step of the invention stated in Example 2 and then subjecting the organic carboxylic acid to the iodide removing step of the invention.

As the present invention may be embodied in various forms without departing from the spirit or the essential characteristics thereof, the above-mentioned examples are therefore illustrative and not restrictive. The scope of the invention is defined by the appended claims rather than by the description preceding them, and all changes that fall within bounds of the claims or equivalences of such bounds are therefore intended to be embraced by the claims.

What is claimed is:

1. A process for preparing an organic carboxylic acid, comprising:

a production step in which alcohol is reacted with carbon monoxide in a reaction solvent in the presence of a rhodium-containing solid catalyst obtained by immobilizing rhodium in an insoluble carrier (I) containing a pyridine ring in its resin structure and an alkyl iodide containing an alkyl group of 1 to 5 carbon atoms, to obtain a reaction product having a water content of 0.5 to 10% by weight; and a removing step in which an organic carboxylic acid is separated and recovered from the reaction product, and the recovered organic carboxylic acid is contacted with an insoluble carrier (II) containing a pyridine ring in its resin structure, to remove an iodide contained in the organic carboxylic acid.

2. The process for preparing an organic carboxylic acid as claimed in claim 1, wherein the insoluble carrier (I) has a pore volume of 0.2 to 0.4 cc/g and a mean pore diameter of 20 to 100 nm.

3. The process for preparing an organic carboxylic acid as claimed in claim 1, wherein the insoluble carrier (I) has a crosslinking degree of 30 to 60%.

4. The process for preparing an organic carboxylic acid as claimed in claim 3, wherein the insoluble carrier (I) has a pore volume of 0.2 to 0.4 cc/g and a mean pore diameter of 20 to 100 nm.

5. The process for preparing an organic carboxylic acid as claimed in claim 1, wherein the insoluble carrier (II) has a pore volume of 0.2 to 0.4 cc/g and a mean pore diameter of 20 to 100 nm.

6. The process for preparing an organic carboxylic acid as claimed in claim 1, wherein the insoluble carrier (II) has a crosslinking degree of 10 to 70%.

7. The process for preparing an organic carboxylic acid as claimed in claim 6, wherein the insoluble carrier (II) has a pore volume of 0.2 to 0.4 cc/g and a mean pore diameter of 20 to 100 nm.

8. The process for preparing an organic carboxylic acid as claimed in claim 1, wherein a partial pressure of the carbon monoxide in the production step is in the range of 7 to 30 $kg/cm^2$-G and a reaction temperature in said step is in the range of 140° to 250° C.

9. The process for preparing an organic carboxylic acid as claimed in claim 8, wherein the insoluble carrier (I) has a crosslinking degree of 30 to 60%.

10. The process for preparing an organic carboxylic acid as claimed in claim 8, wherein the insoluble carrier (I) has a pore volume of 0.2 to 0.4 cc/g and a mean pore diameter of 20 to 100 nm.

11. The process for preparing an organic carboxylic acid as claimed in claim 1, wherein a temperature for contacting the organic carboxylic acid with the insoluble carrier (II) in the removing step is in the range of 40° to 200° C.

12. The process for preparing an organic carboxylic acid as claimed in claim 11, wherein the insoluble carrier (II) has a crosslinking degree of 10 to 70%.

13. The process for preparing an organic carboxylic acid as claimed in claim 11, wherein the insoluble carrier (II) has a pore volume of 0.2 to 0.4 cc/g and a mean pore diameter of 20 to 100 nm.

14. The process for preparing an organic carboxylic acid as claimed in claim 1, wherein a purification step in which an organic carboxylic acid is separated and recovered from the reaction product, and the recovered organic carboxylic acid is contacted with methanol and then further contacted with either an alkali metal hydroxide, an alkali metal salt or a mixture of said hydroxide or said salt with a hypophosphorous acid is carried out after the production step and before the removing step.

* * * * *